United States Patent [19]

Antoun

[11] Patent Number: 6,103,273

[45] Date of Patent: Aug. 15, 2000

[54] PHARMACEUTICAL COMPOSITION COMPRISING STARCH, A COMPOUND COMPRISING BORON, A COMPOUND COMPRISING ZINC, AND WATER, AND A METHOD OF USING SAME TO ENCOURAGE HAIR GROWTH

[76] Inventor: Jacques Antoun, 3630 General de Gaulle Dr., New Orleans, La. 70114

[21] Appl. No.: 08/262,953

[22] Filed: Jun. 21, 1994

Related U.S. Application Data

[63] Continuation-in-part of application No. 07/863,795, Apr. 6, 1992, which is a continuation-in-part of application No. 07/609,392, Nov. 5, 1990, Pat. No. 5,102,916, which is a continuation-in-part of application No. 07/547,460, Jul. 3, 1990, abandoned.

[51] Int. Cl.$^7$ ...................................................... A61K 7/06
[52] U.S. Cl. ............................................ 424/642; 424/701
[58] Field of Search ........................... 424/642, 70, 658, 424/659, 660; 514/880, 881

[56] References Cited

U.S. PATENT DOCUMENTS

| | | | |
|---|---|---|---|
| 124,751 | 3/1872 | Lauer | 424/642 |
| 143,133 | 9/1873 | Fehr | 424/642 |
| 415,208 | 11/1889 | Johnson | 424/642 X |
| 992,937 | 5/1911 | Brodbeck | 424/642 |
| 2,289,125 | 7/1942 | Keil | 424/642 X |
| 2,652,355 | 9/1953 | Ercoli | 424/642 |
| 4,816,254 | 3/1989 | Moss | 424/642 |
| 4,911,932 | 3/1990 | Clum et al. | 424/642 |
| 5,015,470 | 5/1991 | Gibson | 424/70 |

FOREIGN PATENT DOCUMENTS

| | | |
|---|---|---|
| 2653996 | 5/1991 | France . |

*Primary Examiner*—Ralph Gitomer
*Attorney, Agent, or Firm*—Garvey, Smith, Nehrbass & Doody, L.L.C.

[57] ABSTRACT

A pharmaceutical composition for the treatment of alopecia areata and male pattern baldness is preferably made from boric acid, zinc oxide, and starch. The method of the present invention comprises applying the pharmaceutical composition of the present invention to a person's scalp. The pharmaceutical composition of the present invention can comprise 10 parts by weight starch, 60 parts by weight boric acid, 40 parts by weight zinc oxide, and 500 parts by weight water. The dry ingredients (starch, boric acid, and zinc oxide) are mixed together, then the water is added. The mixture is boiled for 20 minutes, stirring continuously. The mixture will thicken, become smooth, and the final consistency will have minute lumps within the liquid. Preferably, before the pharmaceutical composition of the present invention is applied to the scalp, the bald spots are scrubbed with either pure lamb's wool or a soft-bristled brush made of animal hair. This cleanses the residue from the skin. The pharmaceutical composition of the present invention is then rubbed on the bald spots. After 25 minutes, the scalp is rinsed, removing any excess composition. This procedure is repeated daily for 15 days. The inventor has found that it usually takes three–fifteen days for pores to open and fifteen days to three months for fuzzy hair to appear. The inventor has found that it takes approximately one to six months for hair to grow to the point where it appears normal.

24 Claims, No Drawings

PHARMACEUTICAL COMPOSITION COMPRISING STARCH, A COMPOUND COMPRISING BORON, A COMPOUND COMPRISING ZINC, AND WATER, AND A METHOD OF USING SAME TO ENCOURAGE HAIR GROWTH

CROSS REFERENCE TO RELATED APPLICATIONS

This is a Continuation-in-Part of U.S. patent application Ser. No. 07/863,795, filed Apr. 6, 1992, which is a Continuation-in-Part of U.S. patent application Ser. No. 07/609,392, filed Nov. 5, 1990, U.S. Pat. No. 5,102,916, which is a Continuation-in-Part of U.S. patent application Ser. No. 07/547,460, filed Jul. 3, 1990 now abandoned, all of which are hereby incorporated by reference.

SPECIFICATION

BACKGROUND OF THE INVENTION

1. Field of the Invention

The present invention relates to pharmaceutical compositions for and methods of encouraging hair growth.

2. General Background of the Invention

Hair loss occurs in many persons. Two relatively common causes of hair loss are male pattern baldness and alopecia areata. Alopecia areata is a disease affecting about two million people in the United States. It causes hair to fall out quickly, from scattered spots in the size a quarter to complete loss of all bodily hair, including the hair on the scalp. More information about alopecia areata can be obtained from the National Alopecia Areata Foundation (NAAF), P.O. Box 150760, San Rafael, Calif. 94915-0760, (415) 456-4644, Fax: (415) 456-4274. The NAAF publishes a bi-monthly newsletter.

The inventor of the present invention is aware of a commercially available pharmaceutical composition for encouraging hair growth—Rogaine® with minoxidil, commercially available from the Upjohn Company. However, Rogaine® is relatively expensive and has been shown to cause hair regrowth in only about 63% of the women who have tried it (as opposed to 39% of women in a placebo group). According to an August 1991 newspaper article, only 39 percent of men using Rogaine® in clinical trials either grew new hair or stopped losing hair after six to eight months on the drug.

Upjohn advises that at least four months of treatment applying Rogaine twice a day are necessary before results can be seen with it. Further, newly grown hair is usually lost within a few months of stopping treatment with Rogaine.

Dr. Rudolf Japple has reportedly obtained U.S. and foreign patents on the use of the drug diphencyprone in the topical treatment of alopecia areata. The inventor is not aware of the effectiveness of this drug for the treatment of alopecia areata.

Thus, until now, there has been no effective relief for many persons suffering from hair loss due to male pattern baldness or alopecia areata.

Boric acid ($H_3BO_3$) is a mild antiseptic. It also has been used as a germicide. Borax is sodium tetraborate ($Na_2B_4O_7$) and is used as a laundry water softener. Its effect as a water softener is similar to that of ammonia.

Zinc ointment comprises zinc oxide and zinc stearate. Zinc ointment is used for treating various eruptions of the skin. Zinc stearate is an insoluble soap used as a dusting powder for infants. It has antiseptic properties but is irritating to mucous membranes. Zinc undecylenate is used in the treatment of athlete's foot.

U.S. Pat. No. 2,289,125 discloses a topical treatment for fungus infections of the skin in which, among other ingredients, boric acid, zinc oxide and corn starch are used. It is mentioned that the treatment can be mixed with water.

U.S. Pat. No. 2,652,355 describes a fungicidal topical composition in which cornstarch, zinc oxide and boric acid are primary ingredients.

U.S. Pat. No. 4,816,254 discloses an ointment in which boric acid, zinc oxide and gum powder are used to treat irritated skin.

U.S. Pat. No. 124,751 describes a zinc oxide composition to treat dandruff.

U.S. Pat. No. 992,937 discloses a composition in which boric acid, zinc oxide and talc are used to treat irritated skin.

U.S. Pat. No. 4,911,932 discloses a composition in which a composition containing, among other ingredients, borax, zinc oxide and water, is used to treat irritated skin.

None of the cited patents suggest a pharmaceutical composition consisting essentially of a compound comprising boron, a compound comprising zinc, starch, and water. Further, none of the patents suggest using a pharmaceutical composition containing a compound comprising boron, a compound comprising zinc, starch, and water to treat alopecia areata or male pattern baldness.

SUMMARY OF THE INVENTION

The present invention comprises a pharmaceutical composition which has been found to encourage hair growth in humans. The pharmaceutical composition of the present invention consists essentially of water, a compound comprising boron, a compound comprising zinc, and starch $((C_6H_{10}O_5)_x)$. The method of the present invention comprises applying a pharmaceutical composition containing a compound comprising boron, a compound comprising zinc, starch, and water to a person's scalp to treat alopecia areata or male pattern baldness.

Typically, when hair loss is limited to the scalp area, about 30 ml of the pharmaceutical composition is administered topically at least five times per week for three weeks, and is rinsed off approximately 20–30 minutes after being administered topically. More of the pharmaceutical composition is typically used if hair loss is not limited to the scalp area.

The pharmaceutical composition of the present invention can consist essentially of, by weight, 0.143%–3.93% starch, 1.00%–23.8% boron-containing compound, 0.625%–15.8% zinc-containing compound, and the balance water.

Preferably, in the pharmaceutical compound of the present invention and in the pharmaceutical compound used in the method of the present invention, the compound comprising boron is boric acid and the compound comprising zinc is zinc oxide.

One can mix the pharmaceutical composition of the present invention with commercially available shampoo for normal hair to help maintain the work of the pharmaceutical composition between treatments.

DETAILED DESCRIPTION OF THE PREFERRED EMBODIMENT

The pharmaceutical composition of the present invention comprises a zinc-containing compound and a boron-containing compound in a carrier suitable for topical application. Preferably, the zinc-containing compound is zinc oxide, the boron-containing compound is boric acid, and the carrier suitable for topical application is a mixture of starch and water.

The pharmaceutical composition of the present invention is preferably made from starch, zinc oxide, boric acid, and water.

It is believed that the present invention works because the zinc oxide cleans the skin, the boric acid kills germs, and the starch assists in penetration of the zinc oxide and boric acid into the pores of the skin. It is believed by the inventor that the starch stretches the skin to allow the zinc oxide and boric acid to get into the pores of the skin. The starch also acts as a carrier to hold the zinc oxide and boric acid in place on the scalp or other affected area.

It is believed that other zinc compounds may be substituted for zinc oxide, other boron compounds which provide boron ions can be substituted for boric acid, and another carrier could be substituted for starch and water.

The pharmaceutical composition of the present invention can consist essentially of, by weight, 0.143%–3.93% starch, 1.00%–23.8% boron-containing compound, 0.625%–15.8% zinc-containing compound, and the balance water (as in Table 1 when zinc oxide and boric acid are used). More preferably, the pharmaceutical composition of the present invention consists essentially of, by weight, 0.769%–2.73% starch, 5.22%–17.1% boron-containing compound, 3.31%–11.2% zinc-containing compound, and the balance water (as in Table 2 when zinc oxide and boric acid are used). Even more preferably, the pharmaceutical composition of the present invention consists essentially of, by weight, 1.48%–1.86% starch, 9.73%–12.1% boron-containing compound, 6.24%–7.82% zinc-containing compound, and the balance water (as in Table 3 when zinc oxide and boric acid are used).

The present invention also comprises a method of treating alopecia areata or male pattern baldness in a person in need of treatment comprising topically administering to the person in need of treatment a therapeutically effective amount of a pharmaceutical composition comprising water, starch, a compound comprising zinc, and a compound comprising boron.

The pharmaceutical composition used in the method of the present invention comprises 0.143%–3.93% by weight starch, 1.00%–23.8% by weight of the compound comprising boron, 0.625%–15.8% by weight of the compound comprising zinc, and water (as in Table 1 when zinc oxide and boric acid are used). More preferably, the pharmaceutical composition comprises 0.769%–2.73% by weight starch, 5.22%–17.1% by weight of the compound comprising boron, 3.31%–11.2% by weight of the compound comprising zinc, and water (as in Table 2 when zinc oxide and boric acid are used). Even more preferably, the pharmaceutical composition comprises 1.48%–1.86% by weight starch, 9.73%–12.1% by weight of the compound comprising boron, 6.24%–7.82% by weight of the compound comprising zinc, and water (as in Table 3 when zinc oxide and boric acid are used). Preferably, the compound comprising boron is boric acid, and the compound comprising zinc is zinc oxide.

TABLE 1

| | Parts by wt. | % by wt. |
|---|---|---|
| Starch: | 1–20 parts | 0.143%–3.93% |
| Boric acid: | 6–120 parts | 1.00%–23.8% |
| Zinc oxide: | 4–80 parts | .625%–15.8% |
| Water: | 500 parts | 69.4%–97.8% |

TABLE 2

| | Parts by wt. | % by wt. |
|---|---|---|
| Starch: | 5–15 parts | .769%–2.73% |
| Boric acid: | 30–90 parts | 5.22%–17.1% |
| Zinc oxide: | 20–60 parts | 3.31%–11.2% |
| Water: | 500 parts | 75.2%–90.1% |

TABLE 3

| | Parts by wt. | % by wt. |
|---|---|---|
| Starch: | 9–11 parts | 1.48%–1.86% |
| Boric acid: | 54–66 parts | 9.73%–12.1% |
| Zinc oxide: | 36–44 parts | 6.24%–7.82% |
| Water: | 500 parts | 80.5%–83.5% |

To make the pharmaceutical composition of the present invention, the dry ingredients (starch, boron-containing compound, and zinc-containing compound) are mixed together, then the water is added. The mixture is boiled for an appropriate amount of time, stirring continuously.

Preferably, in the pharmaceutical composition of the present invention and in the pharmaceutical composition used in the method of the present invention, the boron-containing compound is boric acid and the zinc-containing compound is zinc oxide.

For example, the pharmaceutical composition of the present invention can comprise 10 parts by weight starch, 60 parts by weight boric acid, 40 parts by weight zinc oxide, and 500 parts by weight water. The dry ingredients (starch, boric acid, and zinc oxide) are mixed together, then the water is added. The mixture is boiled for about 20 minutes, stirring continuously. The mixture will thicken, become smooth, and the final consistency may have minute lumps within the liquid. When a greater quantity of the dry ingredients is used, it may be desirable to boil the mixture for fewer than 20 minutes.

Preferably, before the pharmaceutical composition used in the method of the present invention is applied to the scalp of a subject in need of treatment, the bald spots are scrubbed with either pure lamb's wool or a soft-bristled brush made of animal hair. This cleanses residue from the skin; also, 100% wool is believed to help increase blood circulation. The pharmaceutical composition of the present invention is then rubbed on the bald spots and remains on the affected areas for 5–50 minutes, more preferably 10–40 minutes, even more preferably 20–30 minutes, and most preferably 25 minutes. The affected areas are then rinsed, removing any excess composition. If possible, this procedure is preferably repeated daily for 15 days. Thereafter, the procedure is preferably repeated 4 or 5 times per week for 2 or 3 months. Thereafter, the procedure is preferably repeated 1 or 2 times per week or per month.

The inventor has found that it usually takes three–fifteen days for pores to open and fifteen days to three months for fuzzy hair to appear. The inventor has found that it takes approximately one to six months for hair to grow to the point where it appears normal.

In the United States, four men suffering from alopecia areata have been treated, fourteen men and three women have been treated for male pattern baldness, and two women were treated for hair thinning. Fifteen persons in Lebanon and over ten persons in Spain have also been treated with the method of the present invention. All persons who were treated experienced new hair growth. Four specific examples follow from males treated in the United States. In each of these examples, the subjects were not concurrently treated with any other pharmaceutical composition or drug.

Composition A

|  | Parts by wt. | % by wt. |
| --- | --- | --- |
| Starch: | 10 parts | 1.64% |
| Boric acid: | 60 parts | 9.84% |
| Zinc oxide: | 40 parts | 6.56% |
| Water: | 500 parts | 81.97% |
| Total: | 610 parts | 100% |

EXAMPLE 1

A pharmaceutical composition (Composition A) was made by mixing 10 grams of Argo® pure starch with 60 grams of boric acid obtained from Crystal, Canning Road, Seffner, Fla., and 40 grams of zinc oxide obtained from Humco Laboratory, Texarkana, Tex. 75501, then adding 500 milliliters of water and boiling for 20 minutes, stirring continuously. The composition thickened and became smooth. The final consistency was a colloidal suspension in liquid.

D., a white male, lost about 80% of his hair at the age of 42 years. He also lost hair on his arms and legs. He was diagnosed by a dermatologist as having alopecia areata, and was treated by the dermatologist by being given Quaterzone ointment and injections of cortisone. The treatment lasted one year, but yielded no positive results.

D. was 44 years old at the time the treatment of the present invention began.

D. was treated with Composition A using the method of the present invention. Each treatment consisted of washing the hair and scalp, rinsing, then applying composition A and allowing it to remain on the affected area for about 25 minutes. Initially, he had a treatment six days per week for three weeks. Then, for two or three months, D. had 4 or 5 treatments per week. Thereafter, D. had about a treatment per week for about 15 months. At the age of 46 years, after approximately 220 treatments over 19 months, D. had nearly 100% hair regeneration.

EXAMPLE 2

At the age of 8, F., a white male, was diagnosed with alopecia areata by a medical doctor in the United States. Around the age of 16, F. had an onset of alopecia areata, lost patches of hair on his head and on other parts of his body. Until the age of 19, F. was treated with cortisone injections, Retin A 0.05%, Dithrocreme 0.025%, and Rogaine®, but with limited success. At the age of 20, F. was treated with Composition A, using the method of the present invention.

Initially, he had a treatment six days per week for two months. Then, for six months, F. had 2 or 3 treatments per week. Thereafter, F. had about 4 treatments per week for two or three months. Thereafter, he had a treatment every 3 weeks.

F. had approximately 400 treatments during a period of about three years.

Within eight weeks, F. began to experience regrowth of hair on his scalp and other affected areas. After thirty months, new hair completely covered the affected areas.

EXAMPLE 3

B., a white male, suffering from male pattern baldness, experienced severe thinning over approximately 50% of his scalp (top and rear). B. tried Dejojoba shampoo for six months, and Helsinkey shampoo for six months, but reported that the shampoos helped the hair grow very little.

B. was then treated with Composition A, using the method of the present invention 6 times a week for three weeks. Then, he was treated once per month for about 13 months. He had a total of about 45 treatments over 14 months.

Within three months, B. began to experience regrowth of hair on the affected area of his scalp. The new hair was initially fine, with thicker hair coming in after approximately seven months, the number of hairs per unit area in the affected areas increased to approximately 40%–50% of the rest of the scalp, up from about 10%.

EXAMPLE 4

R., a white male, began losing hair in spots at the age of 26. He lost approximately 20% of the hair on his scalp. He also lost hair on his chin and arm. He was diagnosed by a dermatologist as having alopecia areata, and the dermatologist prescribed Quaterzone. He used Quaterzone for three weeks, without success. He also tried AG Pro, an over-the-counter product, for about a month, but with little improvement.

R. was treated using the method of the present invention, initially receiving 6 treatments per week for 3 weeks. Then, he received 2 treatments per week for 3 months. Thereafter, he received a treatment every 2 or 3 months. About twenty months after beginning treatment (about 40 treatments), R. again has a full head of hair, and the spots where he was missing hair elsewhere on his body have filled in with hair.

As evidenced by the examples presented herein, the pharmaceutical composition of the present invention, produced by the process of the present invention, when applied in accordance with the method of the present invention, can help in the treatment of alopecia areata and male pattern baldness.

Perhaps another suitable carrier could be substituted for starch in the pharmaceutical composition of the present invention.

One can mix the pharmaceutical composition of the present invention (such as Composition A) with commercially available shampoo for normal hair and use every day or every other day. In such a case, the pharmaceutical composition of the present invention preferably comprises 6% to 20% by volume of the mixture of shampoo and pharmaceutical composition. For example, most preferably one can mix 1 part by volume of the pharmaceutical composition of the present invention (such as Compositon A) with 4 parts by volume of commercially available shampoo for normal hair and use every day or every other day. This shampoo of the present invention should be left on the scalp or other affected area for 5–10 minutes, then rinsed off. The shampoo of the present invention can help maintain the work of the pharmaceutical composition between treatments. The shampoo to mix with Composition A could comprise, for example, Quantun shampoo for normal hair, Terma Fuse shampoo for normal hair, or Zachi shampoo for normal hair.

The foregoing embodiments are presented by way of example only; the scope of the present invention is to be limited only by the following claims.

What is claimed is:

1. A pharmaceutical composition comprising 0.143%–3.93% by weight starch, 1.00%–23.8% by weight of a compound comprising boron, 0.625%–15.8% by weight of a compound comprising zinc, and 69.4%–97.8% water.

2. The pharmaceutical composition of claim 1, wherein:
the composition is prepared by boiling a mixture comprising 0.143%–3.93% by weight starch, 1.00%–23.8% by weight of a compound comprising boron, 0.625%–15.8% by weight of a compound comprising zinc, and 69.4%–97.8% water for approximately 20 minutes while stirring continuously.

3. The pharmaceutical composition of claim 1, wherein:
the compound comprising boron is boric acid, and the compound comprising zinc is zinc oxide.

4. The pharmaceutical composition of claim 1, wherein:
the starch comprises 0.769%–2.73% by weight of the composition;
the compound comprising boron comprises 5.22%–17.1% by weight of the composition; and
the compound comprising zinc comprises 3.31%–11.2% by weight of the composition.

5. The pharmaceutical composition of claim 1, wherein:
the starch comprises 1.48%–1.86% by weight of the composition;
the compound comprising boron comprises 9.73%–12.1% by weight of the composition; and
the compound comprising zinc comprises 6.24%–7.82% by weight of the composition.

6. The pharmaceutical composition of claim 1, wherein:
the starch comprises about 1.64% by weight of the composition;
the compound comprising boron comprises 9.84% by weight of the composition; and
the compound comprising zinc comprises 6.56% by weight of the composition.

7. The pharmaceutical composition of claim 6, wherein:
the compound comprising boron is boric acid; and
the compound comprising zinc is zinc oxide.

8. A pharmaceutical composition, consisting essentially of:
starch, a compound comprising boron, a compound comprising zinc, and water.

9. The pharmaceutical composition of claim 8, wherein:
the compound comprising boron is boric acid, and
the compound comprising zinc is zinc oxide.

10. The pharmaceutical composition of claim 8, consisting essentially of:
0.143%–3.93% by weight starch,
1.00%–23.8% by weight of the compound comprising boron,
0.625%–15.8% by weight of the compound comprising zinc, and
water.

11. The pharmaceutical composition of claim 8, consisting essentially of:
0.769%–2.73% by weight starch,
5.22%–17.1% by weight of the compound comprising boron,
3.31%–11.2% by weight of the compound comprising zinc, and
water.

12. The pharmaceutical composition of claim 8, consisting essentially of:
6.24%–7.82% by weight starch,
9.73%–12.1% by weight of the compound comprising boron,
6.24%–7.82% by weight of the compound comprising zinc, and
water.

13. A method of treating alopecia areata or male pattern baldness in a person in need of such treatment comprising:
topically administering to the person in need of treatment a therapeutically effective amount of a pharmaceutical composition comprising a compound comprising zinc, a compound comprising boron, and a suitable carrier for topical application of the pharmaceutical composition, the suitable carrier being a mixture of starch and water.

14. The method of claim 13, wherein the pharmaceutical composition comprises 0.143%–3.93% by weight starch, 1.00%–23.8% by weight of the compound comprising boron, 0.625%–15.8% by weight of the compound comprising zinc, and water.

15. The method of claim 13, wherein the pharmaceutical composition comprises 0.769%–2.73% by weight starch, 5.22%–17.1% by weight of the compound comprising boron, 3.31%–11.2% by weight of the compound comprising zinc, and water.

16. The method of claim 13, wherein the pharmaceutical composition comprises 1.48%–1.86% by weight starch, 9.73%–12.1% by weight of the compound comprising boron, 6.24%–7.82% by weight of the compound comprising zinc, and water.

17. The method of claim 16, wherein:
the compound comprising boron is boric acid, and
the compound comprising zinc is zinc oxide.

18. The method of claim 13 wherein the pharmaceutical composition comprises a solution made by boiling the compound comprising zinc, the compound comprising boron, the starch, and the water.

19. The method of claim 13, wherein:
about 30 ml of the pharmaceutical composition is administered topically at least five times per week for three weeks, and is rinsed off approximately 20–30 minutes after being administered topically.

20. A process of preparing a pharmaceutical composition by boiling a mixture comprising water and 0.143%–3.93% by weight starch, 1.00%–23.8% by weight of a compound comprising boron, 0.625%–15.8% by weight of a compound comprising zinc for approximately 20 minutes while stirring continuously.

21. The product produced by the process of claim 20.

22. The product of claim 21, wherein:
the compound comprising boron is boric acid, and
the compound comprising zinc is zinc oxide.

23. A method of treating alopecia areata or male pattern baldness in a person in need of treatment consisting essentially of:
topically administering to the person in need of treatment an effective amount of the product of claim 21.

24. A composition comprising:
6 percent to 20 percent by volume of the product of claim 21 and the balance shampoo.

* * * * *